(12) United States Patent
Ito

(10) Patent No.: US 11,580,635 B2
(45) Date of Patent: Feb. 14, 2023

(54) FLUID ANALYSIS APPARATUS, METHOD FOR OPERATING FLUID ANALYSIS APPARATUS, AND FLUID ANALYSIS PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 469 days.

(21) Appl. No.: 16/780,915

(22) Filed: Feb. 4, 2020

(65) Prior Publication Data

US 2020/0170520 A1 Jun. 4, 2020

Related U.S. Application Data

(63) Continuation of application No. PCT/JP2018/022330, filed on Jun. 12, 2018.

(30) Foreign Application Priority Data

Sep. 19, 2017 (JP) .............................. JP2017-179169

(51) Int. Cl.
*G06T 7/00* (2017.01)
*A61B 5/026* (2006.01)
(Continued)

(52) U.S. Cl.
CPC .......... *G06T 7/0012* (2013.01); *A61B 5/0263* (2013.01); *A61B 5/0285* (2013.01);
(Continued)

(58) Field of Classification Search
None
See application file for complete search history.

(56) References Cited

U.S. PATENT DOCUMENTS 10,485,508 B2 11/2019 Miyaji et al.
2014/0316758 A1* 10/2014 Yagi .......................... A61F 2/82
703/9

(Continued)

FOREIGN PATENT DOCUMENTS

JP H07213522 8/1995
JP 2007044408 2/2007
(Continued)

OTHER PUBLICATIONS

Gülan, Utku, et al. "Experimental study of aortic flow in the ascending aorta via particle tracking velocimetry." Experiments in fluids 53.5 (2012): 1469-1485. (Year: 2012).*
(Continued)

*Primary Examiner* — Sean M Conner
(74) *Attorney, Agent, or Firm* — JCIPRNET

(57) ABSTRACT

The invention provides a fluid analysis apparatus, a method for operating a fluid analysis apparatus, and a fluid analysis program that perform display such that the tendency of a fluid flow in a blood vessel is easily checked. Route position information that is capable of identifying an order along a route of the anatomical structure is assigned to each position in the anatomical structure, using three-dimensional volume data in which each voxel has the information of a three-dimensional flow velocity vector indicating a flow velocity of a fluid in an anatomical structure. The three-dimensional flow velocity vector is selected such that the route position information of a position where the three-dimensional flow velocity vector is present is sequentially arranged from one point in the anatomical structure and a trajectory indicating the flow of the fluid is drawn so as to be visibly recognized.

21 Claims, 10 Drawing Sheets

(51) Int. Cl.
A61B 5/0285 (2006.01)
A61B 5/055 (2006.01)
G01T 7/00 (2006.01)

(52) U.S. Cl.
CPC .......... *A61B 5/055* (2013.01); *A61B 2576/00* (2013.01); *G01T 7/00* (2013.01); *G06T 2207/30104* (2013.01)

(56) References Cited

U.S. PATENT DOCUMENTS

| 2015/0248758 | A1 | 9/2015 | Pautot |
| 2016/0232660 | A1* | 8/2016 | Bannae .................. G06T 7/215 |

FOREIGN PATENT DOCUMENTS

| JP | 2010125203 | 6/2010 |
| JP | 2015536699 | 12/2015 |
| JP | 2016010425 | 1/2016 |
| JP | 2016214550 | 12/2016 |

OTHER PUBLICATIONS

Sweetman, Brian, and Andreas A. Linninger. "Cerebrospinal fluid flow dynamics in the central nervous system." Annals of biomedical engineering 39.1 (2011): 484-496. (Year: 2011).*

Maniatis, Theofanis A., Richard SC Cobbold, and K. Wayne Johnston. "Flow imaging in an end-to-side anastomosis model using two-dimensional velocity vectors." Ultrasound in medicine & biology 20.6 (1994): 559-569. (Year: 1994).*

"International Search Report (Form PCT/ISA/210) of PCT/JP2018/022330," dated Sep. 4, 2018, with English translation thereof, pp. 1-3.

"Written Opinion of the International Searching Authority (Form PCT/ISA/237) of PCT/JP2018/022330," dated Sep. 4, 2018, with English translation thereof, pp. 1-7.

* cited by examiner

FLUID ANALYSIS APPARATUS, METHOD FOR OPERATING FLUID ANALYSIS APPARATUS, AND FLUID ANALYSIS PROGRAM

CROSS-REFERENCE TO RELATED APPLICATIONS

This application is a Continuation of PCT International Application No. PCT/JP2018/022330 filed on Jun. 12, 2018, which claims priority under 35 U.S.C § 119(a) to Japanese Patent Application No. 2017-179169 filed on Sep. 19, 2017. Each of the above application(s) is hereby expressly incorporated by reference, in its entirety, into the present application.

BACKGROUND OF THE INVENTION

1. Field of the Invention

The present invention relates to a fluid analysis apparatus, a method for operating a fluid analysis apparatus, and a fluid analysis program that display a flow velocity of a fluid in an anatomical structure.

2. Description of the Related Art

In recent years, for example, many studies have been reported which use a blood flow for diagnosis or treatment. For example, a method has been used which checks a blood flow with simulation using a 4D flow technique that four-dimensionally measures the actual blood flow or blood flow analysis using computational fluid dynamics (CFD).

In a case in which the blood flow analysis method using a medical image is used, for example, it is possible to display a flow velocity vector for each voxel, each pixel, or each region on a three-dimensional plane or a two-dimensional plane, using an ultrasound image or a magnetic resonance imaging (MRI) image captured by a three-dimensional cine phase contrast magnetic resonance method. In addition, a method has been proposed which generates a blood vessel model from a CT image or an MRI image captured by administering a contrast agent and performs CFD on the basis of the blood vessel model to calculate a flow velocity vector.

It is desirable to check a blood flow in order to diagnose a heart disease of a patient. In the initial stage of image diagnosis, at the time of conferences or conference presentations, or at the time of patient explanations, it is useful to simply display the entire image of a blood flow in an easy-to-understand manner. Various display methods have been examined. In addition, the display of a streamline, a path line, and a streak line is widely used as a method for three-dimensionally drawing a flow.

JP2010-125203A discloses a method that calculates a two-dimensional velocity vector of each point in the blood vessel on the basis of the information of a blood flow velocity obtained from an ultrasound diagnostic apparatus and estimates the route (for example, a streamline) of a blood flow on the basis of the two-dimensional velocity vector of each point. JP2016-010425A discloses a method that, in a case in which a streamline indicating a blood flow is formed on the basis of the distribution of velocity vectors, traces the blood flow back in a direction opposite to the flow velocity vector to search for a starting point and forms a streamline extending from the starting point. JP2015-536699A discloses a method that, in a case in which a path line is estimated on the basis of a flow velocity vector field estimated from volume data, outputs a path line related to the flow rate of a body fluid in an organ on the basis of the concentration of a contrast agent.

SUMMARY OF THE INVENTION

In the related art, as illustrated in FIG. 12, a method is widely used which displays a vector or a streamline indicating the flow of blood in the blood vessel on a three-dimensional projection image. However, in a case in which the blood vessels overlap each other, a flow different from the actual flow is displayed across the blood vessel wall (see a portion P surrounded by a dashed line).

Accordingly, in order to solve the above-mentioned problems, an object of the invention is to provide a fluid analysis apparatus, a method for operating a fluid analysis apparatus, and a fluid analysis program that perform display such that the tendency of the flow of a fluid, such as blood, is easily checked.

According to the invention, there is provided a fluid analysis apparatus comprising: an assignment unit that acquires, from three-dimensional volume data obtained by capturing an image of an object including an anatomical structure in which a fluid flows, information of a three-dimensional flow velocity vector indicating a flow velocity of the fluid in the anatomical structure for each voxel and assigns route position information capable of identifying an order along a route of the anatomical structure to each position in the anatomical structure; and a drawing unit that selects the three-dimensional flow velocity vector such that route position information of a position where the three-dimensional flow velocity vector is present is sequentially arranged from one point in the anatomical structure and draws a trajectory indicating a flow of the fluid so as to be visibly recognized.

According to the invention, there is provided a method for operating a fluid analysis apparatus comprising an assignment unit and a drawing unit. The method comprises: allowing the assignment unit to acquire, from three-dimensional volume data obtained by capturing an image of an object including an anatomical structure in which a fluid flows, information of a three-dimensional flow velocity vector indicating a flow velocity of the fluid in the anatomical structure for each voxel and to assign route position information capable of identifying an order along a route of the anatomical structure to each position in the anatomical structure; and allowing the drawing unit to select the three-dimensional flow velocity vector such that route position information of a position where the three-dimensional flow velocity vector is present is sequentially arranged from one point in the anatomical structure and to draw a trajectory indicating a flow of the fluid so as to be visibly recognized.

According to the invention, there is provided a fluid analysis program that causes a computer to function as: an assignment unit that acquires, from three-dimensional volume data obtained by capturing an image of an object including an anatomical structure in which a fluid flows, information of a three-dimensional flow velocity vector indicating a flow velocity of the fluid in the anatomical structure for each voxel and assigns route position information capable of identifying an order along a route of the anatomical structure to each position in the anatomical structure; and a drawing unit that selects the three-dimensional flow velocity vector such that route position information of a position where the three-dimensional flow velocity vector is present is sequentially arranged from one point in the anatomical structure and draws a trajectory indicating a flow of the fluid so as to be visibly recognized.

The "anatomical structure" means a structure forming a body such as a tissue or an organ.

In addition, the "three-dimensional volume data" is formed by voxels obtained by finely dividing a three-dimensional space and includes data indicating the flow velocity of a fluid existing at the position of each voxel or physical quantities corresponding to the amount of transmission of radiation or magnetism through organs or tissues. For example, specifically, each voxel has data, such as the value of the flow velocity of a fluid, such as blood, and a concentration value corresponding to an organ or a tissue. The concentration value also includes a concentration value of a fluid, such as blood, included in a tissue, such as a blood vessel. Further, the "three-dimensional flow velocity vector" may be acquired from the value of the flow velocity of each voxel or may be acquired from the amount of movement of the concentration value corresponding to the tissue.

The "route position information capable of identifying the order along the route" may be information for identifying the order of the voxels at the positions along the route or may be, for example, consecutive numbers assigned to the voxels along the route. The term "selecting the three-dimensional flow velocity vector such that the route position information is sequentially arranged" means selecting the voxel whose route position information monotonously increases (or decreases) along the route and acquiring the three-dimensional flow velocity vector of each voxel. In the selection of the voxel such that the route position information is sequentially arranged, the voxels may be selected as follows: even in a case in which the selected voxels are not consecutive numbers, voxels at the positions where the distance between two points on the route along the route is equal to or greater than a predetermined value may not be selected and voxels having the route position information that monotonously increases (or decreases) in a case in which the voxel is traced along the route may be selected. The route position information is information indicating the position along the route on the basis of information indicating the anteroposterior relationship between the information at a branching point or a joining point of the route.

The term "drawing the trajectory indicating the flow of the fluid so as to be visibly recognized" may be any aspect in which the trajectory indicating the flow of the fluid can be visibly recognized and may be an aspect in which, even in a case in which the trajectory is represented by a line, each particle forming the fluid is drawn such that the movement aspect of the particles can be visibly recognized.

The assignment unit may extract a center line of the anatomical structure, assign route position information along the center line, and assign the same route position information as the route position information assigned to the center line to each position in a cross section perpendicular to the center line of the anatomical structure.

The assignment unit may assign the same route position information as the route position information assigned along the center line of the anatomical structure closest to the three-dimensional flow velocity vector in the anatomical structure.

The drawing unit may draw the trajectory on a morphological image obtained by projecting a morphology of the anatomical structure to a projection plane so as to be visibly recognized.

Before and after a connection portion in which the anatomical structure is branched or joins, the assignment unit may assign relative position information indicating a connection relationship between a route before the branching and a plurality of routes after the branching or a connection relationship between a plurality of routes before the joining and a route after the joining. The drawing unit may draw the trajectory so as to be visibly recognized on the basis of the route position information and the relative position information.

The three-dimensional flow velocity vector may be obtained from three-dimensional volume data captured by a three-dimensional cine phase contrast magnetic resonance method.

The anatomical structure may be a blood vessel, the fluid may be blood, and the three-dimensional flow velocity vector may be a flow velocity vector of the blood.

The three-dimensional flow velocity vector may be obtained by a result of a blood flow analysis simulation.

The fluid may be cerebrospinal fluid and the three-dimensional flow velocity vector may be a flow velocity vector of the cerebrospinal fluid.

The trajectory may be a streamline, a path line, or a streak line.

The trajectory may be drawn by a particle tracking method.

Another fluid analysis apparatus according to the invention comprises a memory that stores commands to be executed by a computer and a processor that is configured to execute the stored commands. The processor performs a process of acquiring, from three-dimensional volume data obtained by capturing an image of an object including an anatomical structure in which a fluid flows, information of a three-dimensional flow velocity vector indicating a flow velocity of the fluid in the anatomical structure for each voxel and assigning route position information capable of identifying an order along a route of the anatomical structure to each position in the anatomical structure and a process of selecting the three-dimensional flow velocity vector such that route position information of a position where the three-dimensional flow velocity vector is present is sequentially arranged from one point in the anatomical structure and drawing a trajectory indicating a flow of the fluid so as to be visibly recognized.

According to the invention, route position information that is capable of identifying an order along a route of the anatomical structure is assigned to each position in the anatomical structure, using three-dimensional volume data in which each voxel has the information of a three-dimensional flow velocity vector indicating the flow velocity of a fluid in an anatomical structure. The three-dimensional flow velocity vector is selected such that the route position information is sequentially arranged from one point in the anatomical structure and a trajectory indicating the flow of the fluid is drawn so as to be visibly recognized. Therefore, even in a case in which the routes of the anatomical structures intersect each other, a flow that does not follow the route of the structure is not displayed. As a result, it is possible to quickly and intuitively check a three-dimensional flow tendency.

DESCRIPTION OF THE PREFERRED EMBODIMENTS

Figure 1:
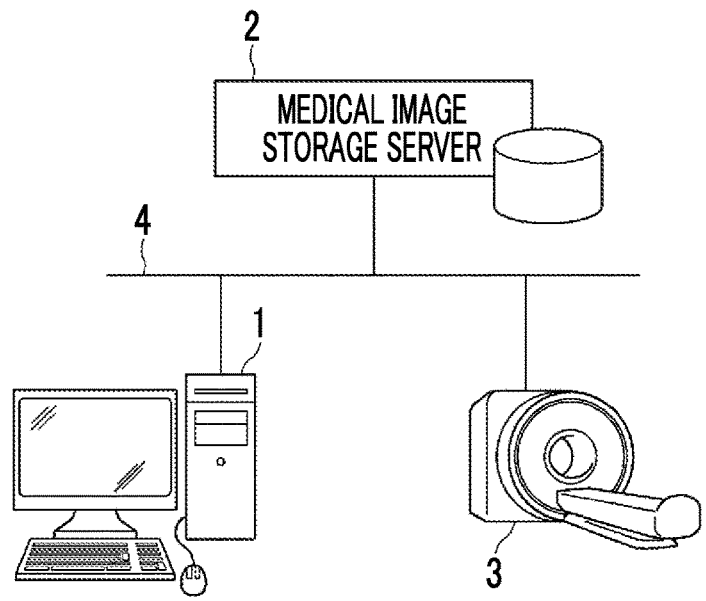
FIG. 1 is a diagram schematically illustrating the configuration of a medical information system.

Hereinafter, a medical information system comprising a fluid analysis apparatus 1 according to a first embodiment of the invention will be described with reference to the drawings. FIG. 1 is a block diagram schematically illustrating the configuration of the medical information system according to this embodiment.

Specifically, as illustrated in FIG. 1, the medical information system according to this embodiment is configured by connecting the fluid analysis apparatus 1, a medical image storage server 2, and an imaging apparatus 3 (hereinafter, referred to as a modality) through a network 4 so as to communicate with each other.

The modality 3 is, for example, a computed tomography (CT) apparatus, a magnetic resonance imaging (MRI) apparatus, or an ultrasonography apparatus. Captured three-dimensional volume data is transmitted to the medical image storage server 2 through the network 4 according to a storage format based on a digital imaging and communication in medicine (DICOM) standard and a communication standard and is then stored therein.

The fluid analysis apparatus 1 is a general-purpose computer and comprises known hardware configurations, such as a central processing unit (CPU), a memory (main storage device), a storage (auxiliary storage device), an input/output interface, a communication interface, an input device, a display device, and a data bus. For example, a known operation system is installed in the fluid analysis apparatus 1. In addition, for example, the fluid analysis apparatus 1 has a liquid crystal display as the display device and has a pointing device, such as a keyboard and/or a mouse, as the input device. The storage is, for example, a hard disk drive or a solid state drive (SSD). In addition, a computer may be provided with a graphics processing unit (GPU) if necessary. A fluid analysis program according to this embodiment is installed in the computer. The computer executes the fluid analysis program to function as the fluid analysis apparatus 1. Further, the fluid analysis apparatus 1 has a function of requesting the medical image storage server 2 to transmit an image and a function of receiving an image from the medical image storage server 2 and executes a software program for each function to perform the functions.

The fluid analysis program is recorded on a recording medium, such as a digital versatile disc (DVD) or a compact disc read only memory (CD-ROM), and is then distributed. The fluid analysis program is read from the recording medium and is installed in the computer. Alternatively, the fluid analysis program may be stored in a storage device of a server computer connected to the network or a network storage such that it can be accessed from the outside, may be downloaded to the computer in response to a request from the outside, and may be installed.

Figure 2:
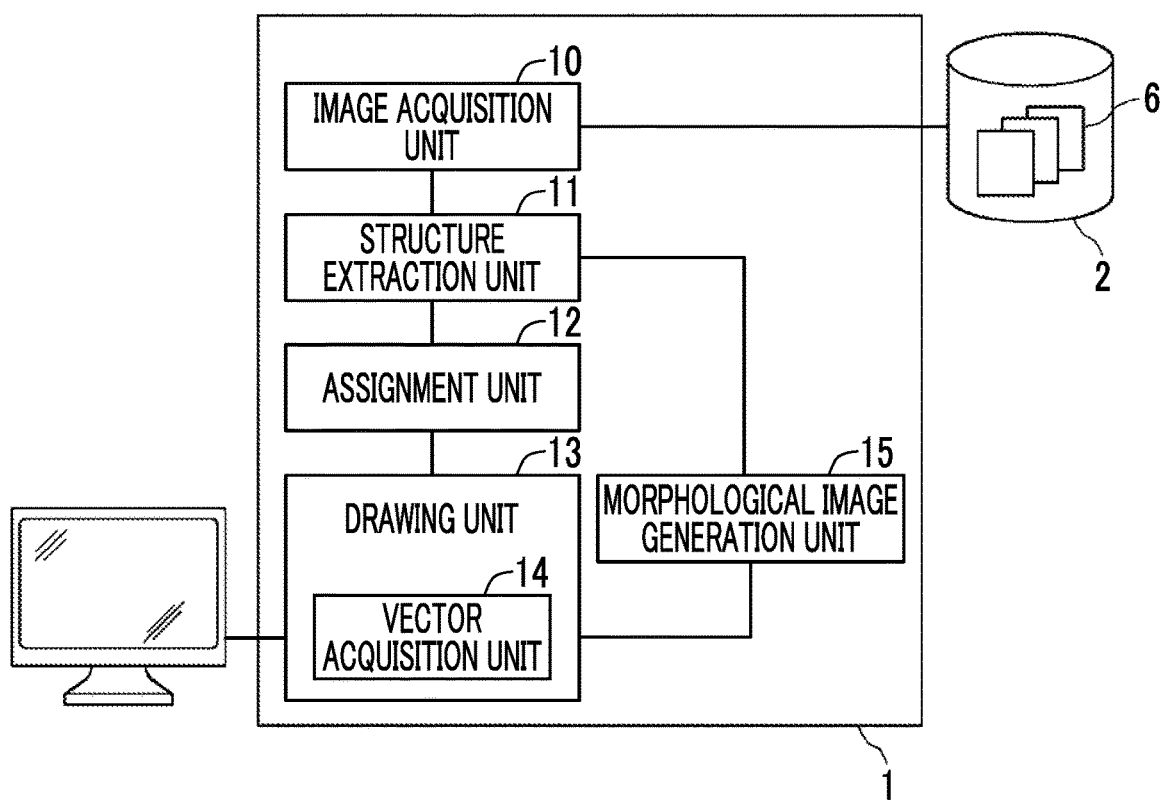
FIG. 2 is a diagram schematically illustrating the configuration of a fluid analysis apparatus according to a first embodiment of the invention.

As illustrated in FIG. 2, the fluid analysis apparatus 1 comprises an image acquisition unit 10, a structure extraction unit 11, an assignment unit 12, a drawing unit 13, and a morphological image generation unit 15.

The image acquisition unit 10 acquires three-dimensional volume data 6 of a patient which has been captured in advance. In this embodiment, the three-dimensional volume data 6 is data captured by, for example, a CT apparatus, an MRI apparatus, or an ultrasonography apparatus.

The three-dimensional volume data 6 is stored in advance in the medical image storage server 2 together with the identification information of the patient. The image acquisition unit 10 reads one or more kinds of three-dimensional volume data 6 having the identification information of the patient from the medical image storage server 2 on the basis of the identification information of the patient input by the user through an input device, such as a keyboard, and stores the read three-dimensional volume data 6 in the storage (not illustrated). In addition, the three-dimensional volume data 6 is a CT image, a contrast-enhanced CT image, an MRI image, a contrast-enhanced MRI image, or volume data captured by a three-dimensional cine phase contrast magnetic resonance method (3D cine PC MRI). In this embodiment, a case in which a plurality of kinds of three-dimensional volume data obtained by capturing the image of the same part of the same patient are stored in the storage will be described.

The structure extraction unit 11 extracts an anatomical structure from the three-dimensional volume data 6. A structure in which a fluid flows is a tubular structure such as a blood vessel. Hereinafter, in this embodiment, a case in which the image acquisition unit 10 acquires the three-dimensional volume data 6 of the chest of the patient, the anatomical structure is a blood vessel, and the fluid is blood will be described. Hereinafter, the structure extraction unit 11 is described as a blood vessel region extraction unit 11.

The blood vessel region extraction unit 11 extracts a blood vessel region (a region of the anatomical structure) from the three-dimensional volume data 6. Specifically, the blood vessel region is extracted using a CT image (or a contrast-enhanced CT image) or an MRI image (or a contrast-enhanced MRI image). A case in which the blood vessel region extraction unit 11 according to this embodiment extracts a blood vessel region from the CT image of the chest will be described. For example, the blood vessel region extraction unit 11 performs multi-resolution conversion for the three-dimensional volume data 6 of the chest to generate a plurality of images with different resolutions and performs eigenvalue analysis for the images with each resolution using a Hessian matrix to extract a line structure. In addition, the blood vessel region extraction unit 11 integrates the analysis results of the images with each resolution and extracts a blood vessel region as an aggregate of line structures with various sizes in a chest region (for example, see Y Sato, et al., "Three-dimensional multi-scale line filter for segmentation and visualization of curvilinear structures in medical images.", Medical Image Analysis, June 1998, Vol. 2, No. 2, p.p. 143-168). Furthermore, the blood vessel region extraction unit 11 connects center lines of the extracted line structures using, for example, a minimum spanning tree algorithm to generate tree structure data indicating a blood vessel. Alternatively, the blood vessel region extraction unit 11 may calculate cross sections orthogonal to a core line at each point on the core line connecting the center lines of the blood vessels, recognize the contour of the blood vessel in each cross section, and extract a blood vessel region on the basis of information indicating the contour, using a known segmentation method such as a graph cut method.

A method for extracting the blood vessel region is not limited to the above-mentioned method and other known methods, such as a region expansion method, may be used.

The assignment unit 12 assigns route position information that can identify the order of positions along a blood vessel route to each position in the blood vessel.

Figure 3:
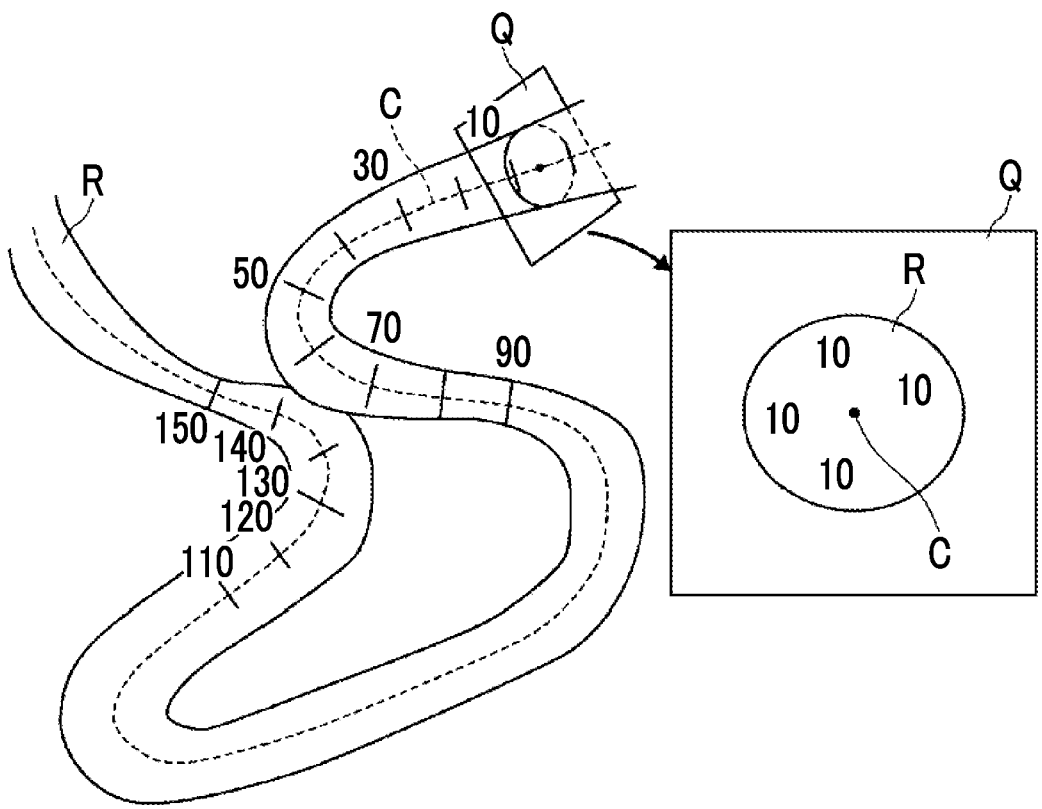
FIG. 3 is a diagram illustrating a method for assigning route position information.

First, as illustrated in FIG. 3, a center line C of the blood vessel region extracted by the blood vessel region extraction unit 11 is extracted. The route position information that is uniquely determined is sequentially assigned to each voxel of the center line C along the route. Specifically, as the route position information, consecutive numbers are sequentially assigned from a predetermined point on the center line C. For example, as the route position information, numbers are assigned in the order of 1, 2, 3, . . . along the route. FIG. 3 illustrates an example in which numbers are assigned in increments of 10. A vertical cross section Q is set at each position of the center line C of the blood vessel region R and the same route position information as the route position information of the center line C is assigned to all of the voxels in the blood vessel region R. As illustrated in an enlarged view on the right side of FIG. 3, in a case in which the route position information of the voxel corresponding to the center line C is "10", all of the route position information items of the voxels in the blood vessel region R included in the vertical cross section Q are "10".

Figure 4:
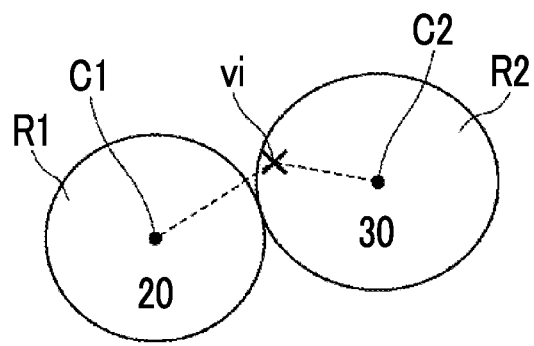
FIG. 4 is a diagram illustrating a method for assigning the route position information in two blood vessel regions.

As illustrated in FIG. 4, in a place where two blood vessel regions R1 and R2 are adjacent to each other, the route position information of a blood vessel region having the shorter distance from each voxel vi to the center lines C1 and C2 of the two blood vessel regions R1 and R2 is assigned to the voxels of the blood vessel region. FIG. 4 illustrates a case in which the route position information of the voxel in the vertical cross section of the center line C1 is "20" and the route position information of the voxel in the vertical cross section of the center line C2 is "30". Of the distance from the voxel vi to the center line C1 and the distance from the voxel vi to the center line C2, the distance from the voxel vi to the center line C2 is short. Therefore, the route position information of the voxel vi is "30".

Figure 5A:
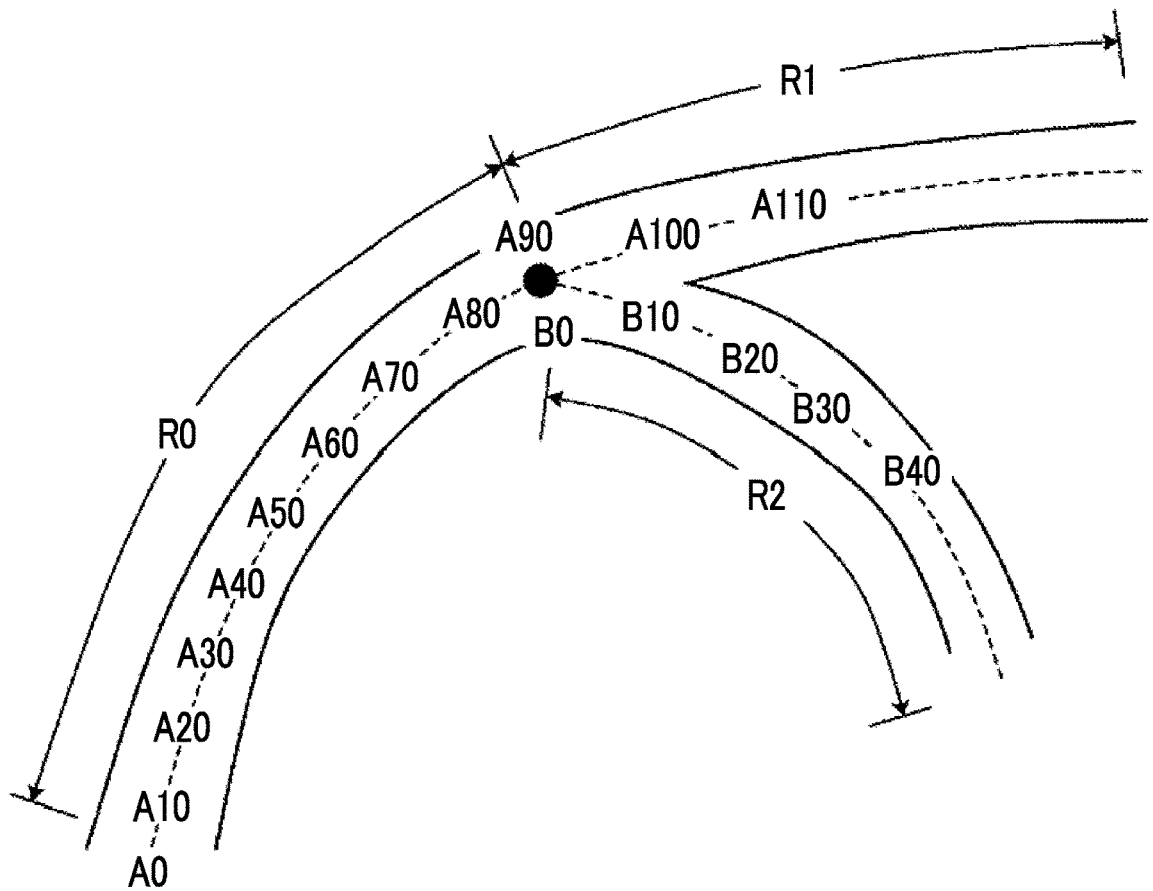
FIG. 5A is a diagram illustrating a method for assigning the route position information in a portion in which the blood vessel is branched.
Figure 5B:
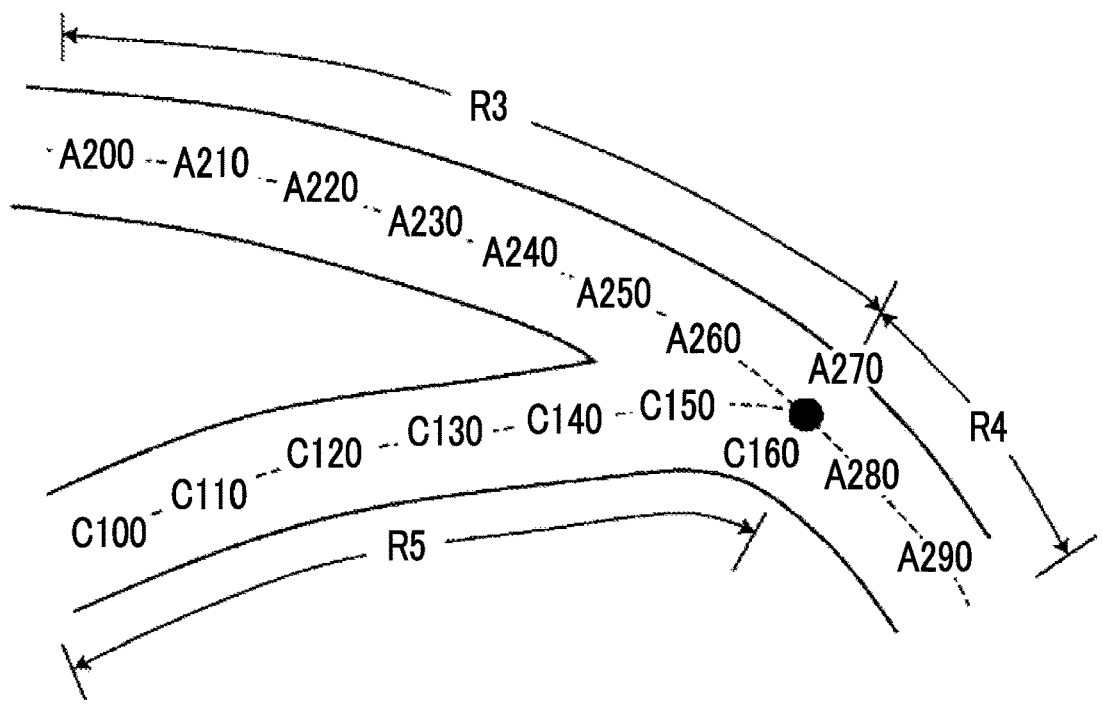
FIG. 5B is a diagram illustrating a method for assigning the route position information in a portion in which the blood vessel joins.

In a connection portion in which the blood vessel is branched into two routes as illustrated in FIG. 5A or in a connection portion in which two blood vessels join as illustrated in FIG. 5B, the route position information is discontinuous and it is difficult to identify the order of the route position information in the connection portion. Therefore, relative position information indicating the connection relationship between a route before branching and a plurality of routes after branching or the connection relationship between a plurality of routes before joining and a route after joining is recorded.

In the example illustrated in FIG. 5A, continuous route position information items are assigned to a blood vessel region R0 and a blood vessel region R1 and consecutive numbers are sequentially allocated from "A0". In a blood vessel region R2 after the blood vessel is branched, new route position information "BO" is assigned from a connection portion "A90" and consecutive numbers are sequentially allocated from "BO". "A90" and "BO" are connection portions and are recorded as relative position information indicating that a route before branching and a plurality of routes after branching are connected in the branch portion. In the example illustrated in FIG. 5A, the blood vessel region R0 and the blood vessel region R2 are connected at "A90" of the blood vessel region R0 and "BO" of the blood vessel region R2 and relative position information indicating that the blood vessel is branched into two routes from the connection portion is recorded.

In the example illustrated in FIG. 5B, continuous route position information items are assigned to a blood vessel region R3 and a blood vessel region R4 and consecutive numbers are sequentially allocated from "A200". A blood vessel region R5 is a blood vessel that joins the blood vessel and consecutive numbers are sequentially allocated from first route position information "C100". The blood vessel region R5 joins "A270" of the blood vessel region R4 at "C160". In the example illustrated in FIG. 5B, the blood vessel region R3 and the blood vessel region R4 are connected at "A270" of the blood vessel region R3 and "C160" of the blood vessel region R4 and relative position information indicating that the two blood vessels join is recorded.

The drawing unit 13 further comprises a vector acquisition unit 14 (see FIG. 2) and performs drawing such that a blood flow can be recognized according to the route position information and relative position information of the voxels assigned by the assignment unit 12 and the direction of the three-dimensional flow velocity vector acquired by the vector acquisition unit 14 and displays the blood flow on a display device. Specifically, for example, the drawing unit 13 may draw and display a trajectory indicating a blood flow. Examples of the trajectory include a streamline, a path line, or a streak line. The streamline is a line that smoothly connects blood velocity vectors from the position of a starting point, the path line is a trajectory in which one fluid particle moves over time, and the streak line is a line that can connect all fluid particles passing through a fixed point in a flow. Alternatively, as a method that performs drawing capable of recognizing the trajectory indicating the blood flow, a method of visualizing the movement of particles in a velocity field, such as particle tracking or particle tracer, may be used to perform drawing such that a blood flow can be recognized.

The vector acquisition unit 14 acquires a three-dimensional flow velocity vector indicating the flow velocity and flow direction of blood in the blood vessel region. The three-dimensional flow velocity vector can be acquired by various methods. For example, the image acquisition unit 10 acquires the three-dimensional volume data captured by the three-dimensional cine phase contrast magnetic resonance method and the three-dimensional flow velocity vector is acquired using velocity information in the blood vessel region acquired on the basis of the three-dimensional volume data.

Figure 6:
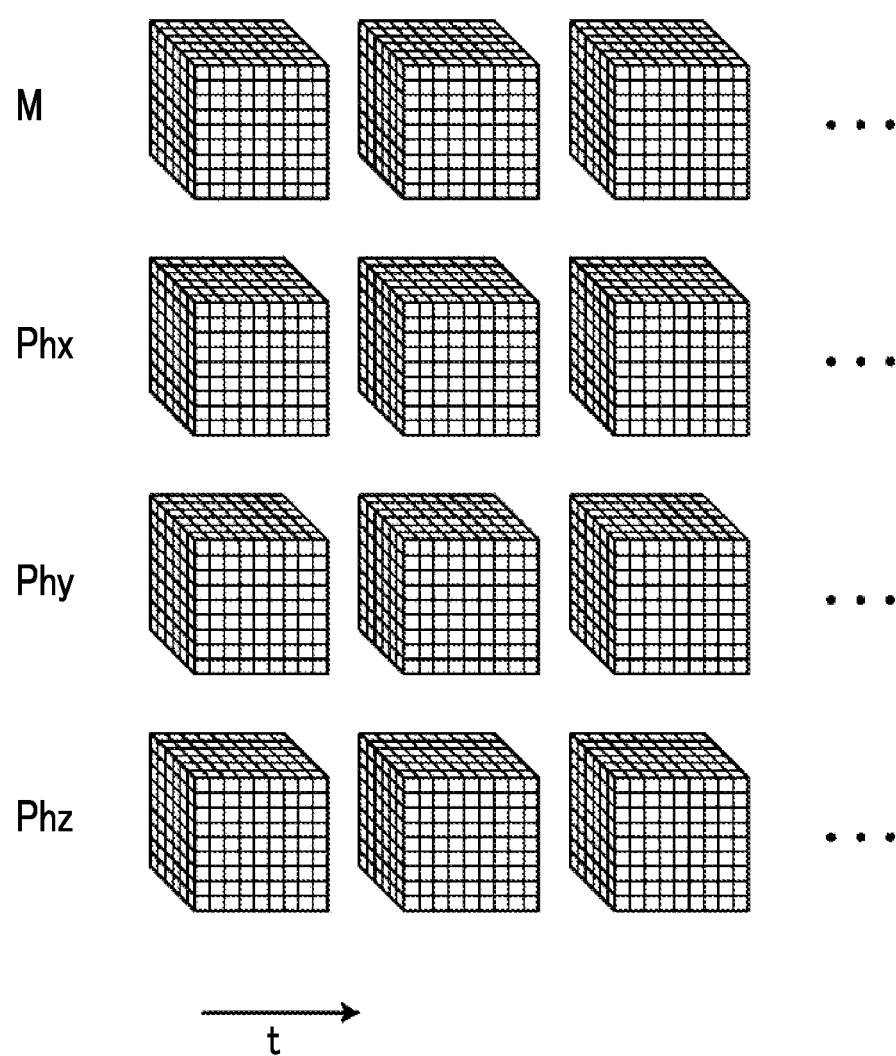
FIG. 6 is a diagram illustrating volume data captured by a three-dimensional cine phase contrast magnetic resonance method.

As illustrated in FIG. 6, the volume data captured by the three-dimensional cine phase contrast magnetic resonance method is volume data obtained by arranging magnitude data M and phase data Phx in the X-axis direction, phase data Phy in the Y-axis direction, and phase data Phz in the Z-axis direction subjected to encoding (velocity encoding (VENC)) in the X-axis direction, the Y-axis direction, and the Z-axis direction which are arranged in a predetermined cycle (for example, a cardiac cycle) along time t. The phase data Phx in the X-axis direction, the phase data Phy in the Y-axis direction, and the phase data Phz in the Z-axis direction indicate flow velocities in each axis direction. The three-dimensional flow velocity vector at each voxel position is obtained from three phase data items.

Then, the CT image from which the blood vessel region has been extracted by the blood vessel region extraction unit 11 and each of the phase data Phx, the phase data Phy, and the phase data Phz captured by the three-dimensional cine phase contrast magnetic resonance method are aligned such that the same positions correspond to each other. The CT image and the volume data of each phase data may be aligned with each other by a known method such as a method for aligning feature points of an imaging part. For the three-dimensional flow velocity vector in the blood vessel region, velocity components in each axis direction are obtained from each voxel of each of the phase data Phx, the phase data Phy, and the phase data Phz corresponding to the position of the voxel in the blood vessel region on the basis of the extraction result of the blood vessel region extraction unit 11 and the three-dimensional flow velocity vector is acquired. Hereinafter, a specific example of a case in which the three-dimensional flow velocity vector in the blood vessel region is acquired on the basis of the volume data captured by the three-dimensional cine phase contrast magnetic resonance method using the MRI apparatus will be described.

Figure 7A:
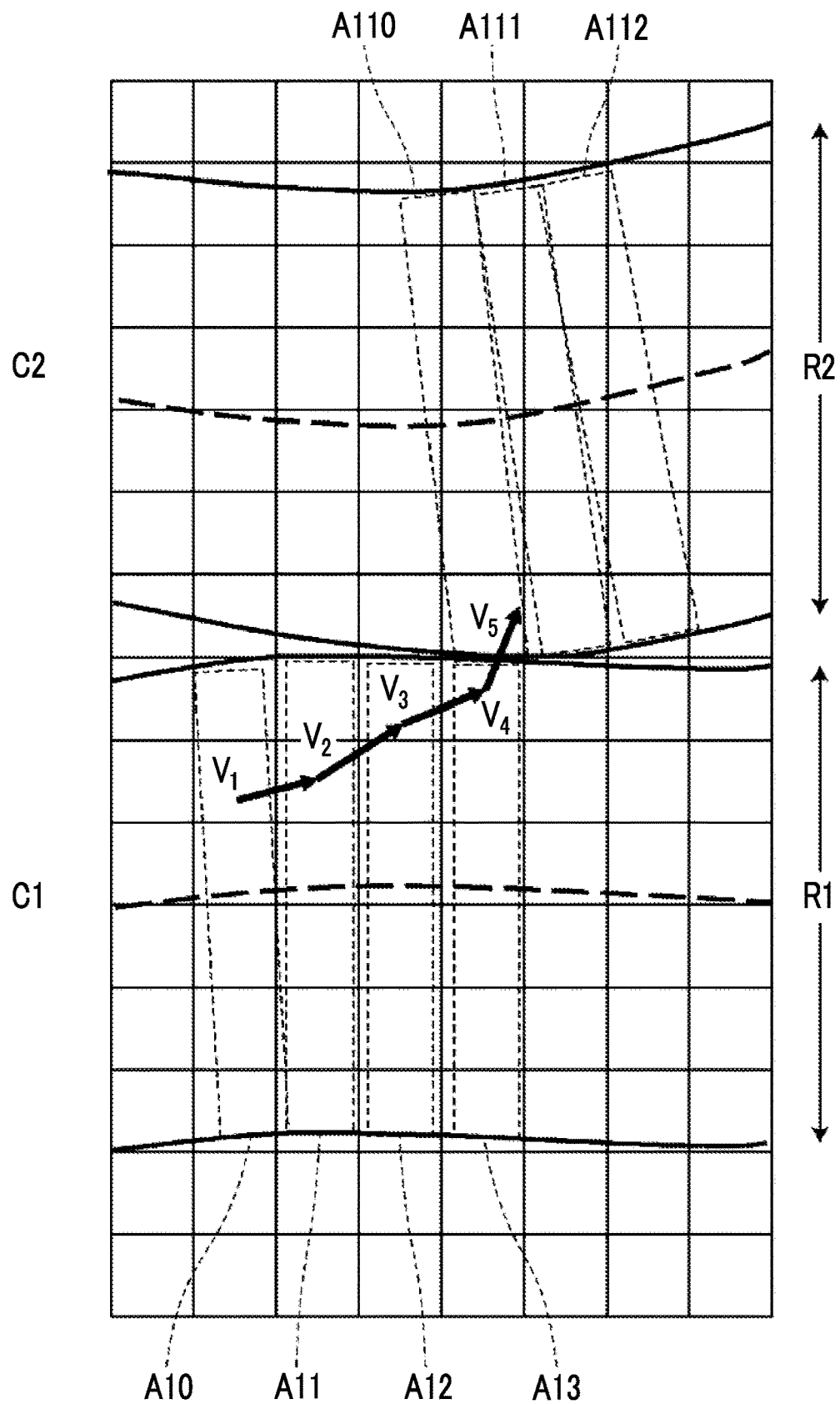
FIG. 7A is a diagram illustrating a method for tracing a voxel in order to draw a trajectory.

Next, a method for performing drawing such that a blood flow can be recognized according to the three-dimensional flow velocity vector acquired by the vector acquisition unit 14 in the drawing unit 13 will be described in detail. Here, a drawing method will be described using the streamline as an example. First, one point in the blood vessel region is selected as a starting point and a streamline is generated while tracing voxels with continuous route position information items according to the three-dimensional flow velocity vector of each voxel. A method of tracing voxels will be described with reference to FIG. 7A. In FIG. 7A, the description will be made using voxels that are two-dimensionally illustrated for convenience. In FIG. 7A, a grid indicates one voxel and an arrow indicates a flow velocity vector direction. A dashed line frame indicates the range of the voxels included in one section of the cross section perpendicular to the center line C1 of the blood vessel region R1 or the center line C2 of the blood vessel region R2. The same route position information is assigned to the dashed line frame. First, a case in which the drawing of a streamline starts from a voxel vi will be described. The route position information of the voxel vi is "A10". A voxel subsequent to the voxel vi is a voxel $v_2$ in the direction indicated by the flow velocity vector from the voxel vi. The route position information of the voxel $v_2$ is "A11" and the route position information items of the voxel $v_1$ and the voxel $v_2$ are continuous. That is, since the route position information is arranged along the route, it is determined that the voxel $v_2$ is in the blood vessel region R1 and a streamline connecting the streamline vectors of the voxel vi and the voxel $v_2$ is generated. A voxel subsequent to the voxel $v_2$ is a voxel $v_3$ that is located ahead of the voxel $v_2$ in the direction indicated by the flow velocity vector. The route position information of the voxel $v_3$ is "A12" and the route position information items of the voxel $v_2$ and the voxel $v_3$ are sequentially arranged. Therefore, it is determined that the voxel $v_3$ is in the blood vessel region R1. Therefore, a streamline connecting the streamline vectors of the voxel $v_2$ and the voxel $v_3$ is generated and the generated streamline connecting the streamline vectors of the voxel vi and the voxel $v_2$ is extended. Similarly, the route position information of a voxel $v_4$ subsequent to the voxel $v_3$ is "A13" and the route position information items of the voxel $v_3$ and the voxel $v_4$ are continuous. Therefore, it is determined that the voxel $v_4$ is in blood vessel region R1. A streamline connecting the streamline vectors of the voxel $v_3$ and the voxel $v_4$ is generated and the generated streamline is extended.

A voxel subsequent to the voxel $v_4$ is a voxel $v_5$ in the direction indicated by the flow velocity vector from the voxel $v_4$ and the route position information of the voxel $v_5$ is "A110" and is not route position information that is continuous with the route position information "A13" of the voxel $v_4$. The route position information items of the voxels $v_4$ and $v_5$ are "A13" and "A110", respectively, and the sections along the route are 96 sections apart. In a case in which there are 96 sections between two points, the distance between the two points (the distance on the center line) along the route is considered to be quite long. Therefore, it is considered that the voxel $v_5$ is not located in the same blood vessel region R1 as the voxel vi, but is located in the blood vessel region R2. Therefore, it is determined that the position of the voxel $v_5$ is not in the same blood vessel region R1, but is in the adjacent blood vessel region R2. Therefore, the end point of the streamline starting from the voxel $v_1$ is the voxel $v_4$.

Figure 7B:
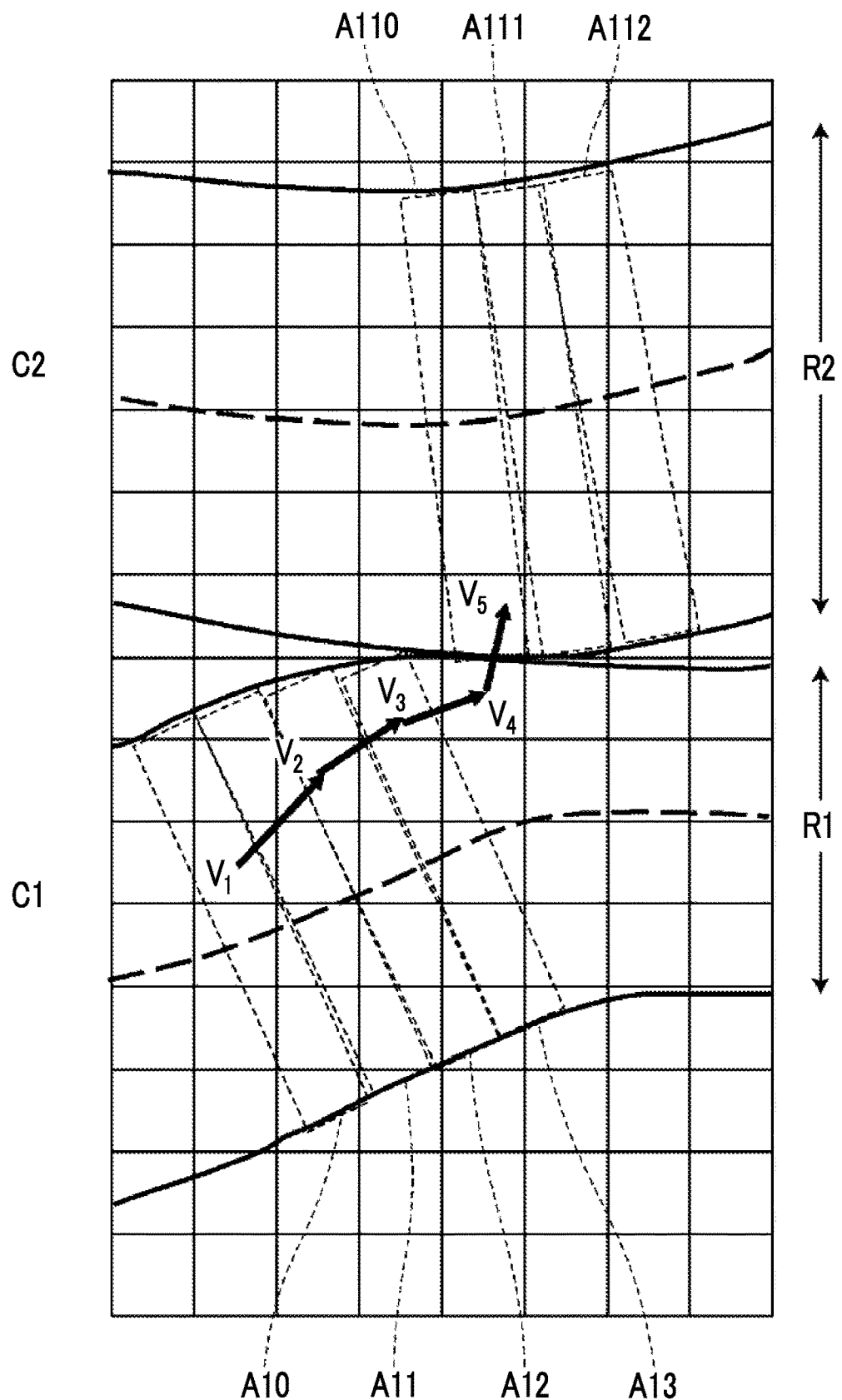
FIG. 7B is a diagram illustrating a method for tracing a voxel in order to draw a trajectory.

In a case in which the relationship between the direction of the blood vessel route and the voxels is as illustrated in FIG. 7B, the route position information items may be in the same blood vessel region R1, depending on the inclination of the route and the position of the voxels, even though the values of the route position information items are not continuous. The route position information of the first voxel vi is "A10". However, the route position information of the next voxel $v_2$ in the direction indicated by the flow velocity vector of the voxel vi may be "A12". In this case, it is determined that the route position information items are not continuous, but are sequentially arranged. For example, in some cases, the route position information of the voxel $v_2$ is a number before or after the route position information "A11" that is continuous with the route position information "A10" of the voxel vi, for example, the route position information "A10" or "A12" close to "A11". Since the route position information items of the voxels $v_1$ and $v_2$ are "A10" and "A12", respectively, and are only one section apart, they are considered to be located in the blood vessel region R1. Therefore, a streamline connecting the flow velocity vectors of the voxels vi and the voxel $v_2$ is generated. As such, in a case in which the route position information of the next voxel traced from one voxel can be determined to be within the same blood vessel region R1 from the size of the voxels and the width of the blood vessel even though the route position information items are not consecutive numbers, a streamline connecting the flow velocity vectors of two voxels is generated.

In a case in which a streamline is created by tracing the voxels as described above, it is determined that the distance between two voxels along the route is equal to or greater than a predetermined value on the basis of the route position information of each voxel to determine whether the voxels are within another adjacent blood vessel region.

Figure 8:
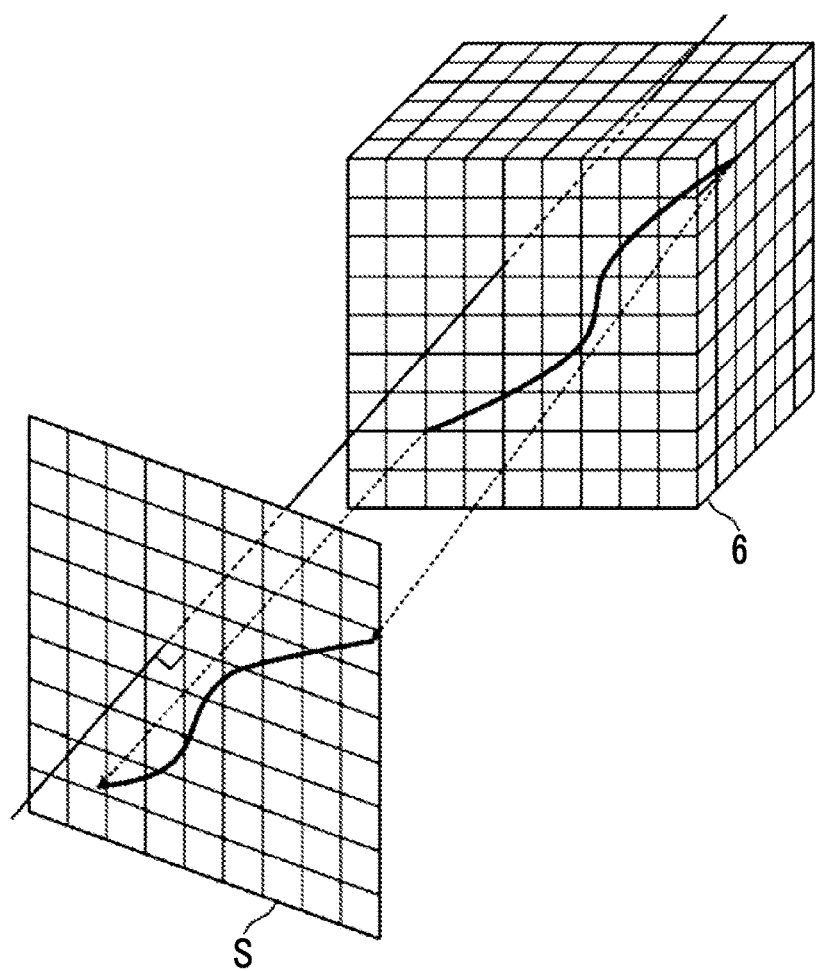
FIG. 8 is a diagram illustrating a state in which a streamline generated by tracing the voxel is projected to a projection plane.

A method for drawing a streamline on a two-dimensional plane has been described above. However, in practice, the drawing unit 13 displays an image obtained by projecting the streamline generated by tracing each voxel of three-dimensional volume data 6 to a projection plane S on the display device as illustrated in FIG. 8.

The case in which the route position information monotonously increases along the route has been described above. However, the route position information may monotonously decrease along the route.

Figure 9:
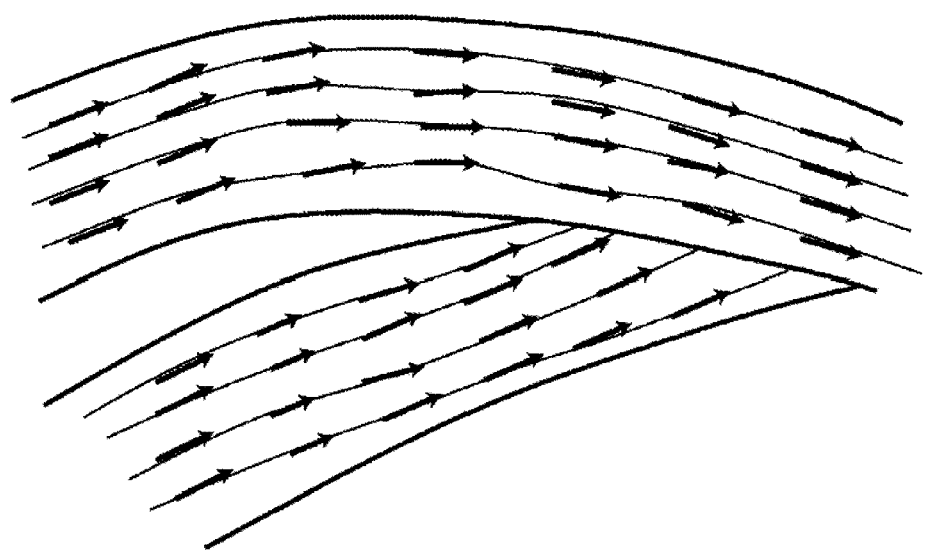
FIG. 9 illustrates an example of the drawing of the streamline.
Figure 12:
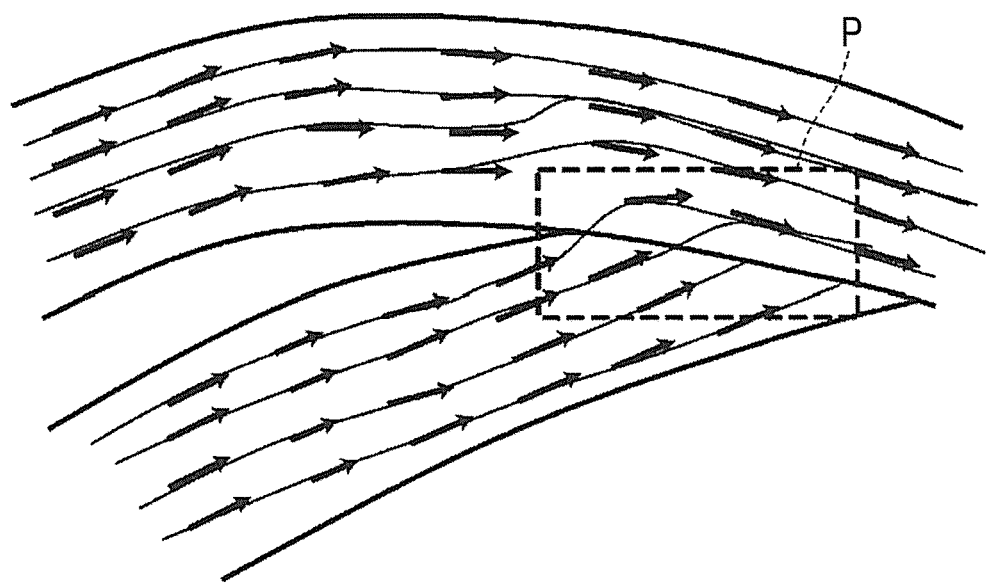
FIG. 12 illustrates an example of the display of a streamline according to the related art.

FIG. 9 illustrates an example in which a streamline is drawn by the above-mentioned method. In the method according to the related art illustrated in FIG. 12, a streamline that has penetrated through the blood vessel wall can be ended before the blood vessel wall by the method according to the embodiment of the invention as in a portion P surrounded by a dashed line.

Figure 10A:
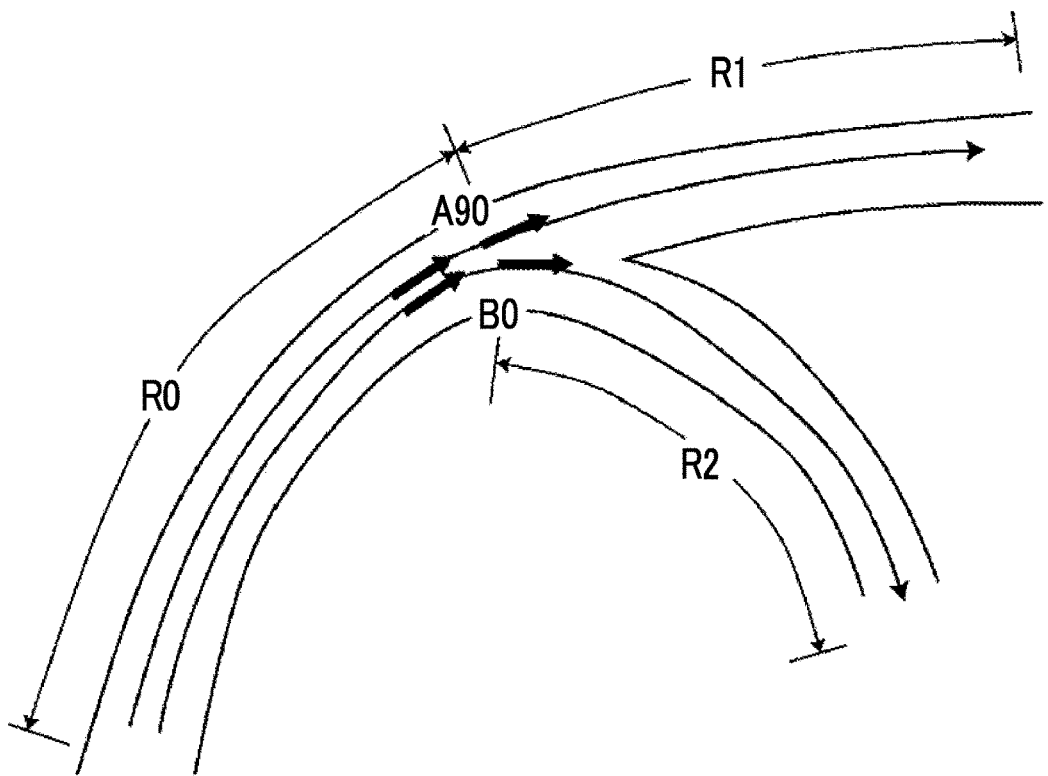
FIG. 10A illustrates an example of the streamline in a case in which the blood vessel is branched.

Next, a portion in which the blood vessel is branched will be described. As illustrated in FIG. 5A, "A90" and "B0" are connection portions and the voxels to which route position information following "A90" is assigned and the voxels to which route position information following "B0" is assigned are present in the vicinity of the connection portions. It is determined whether the streamline connected first from "A90" and "B0" is a streamline connected in a direction from the blood vessel region R0 to the blood vessel region R1 or a streamline connected in a direction from the blood vessel region R0 to the blood vessel region R2, according to whether there is a voxel to which route position information following "B0" is assigned or there is a voxel to which route position information following "A90" is assigned in the direction indicated by the three-dimensional flow velocity vector of each voxel. FIG. 10A illustrates an example in which the streamline is divided into two blood vessels from the connection portions "A90" and "B0".

Figure 10B:
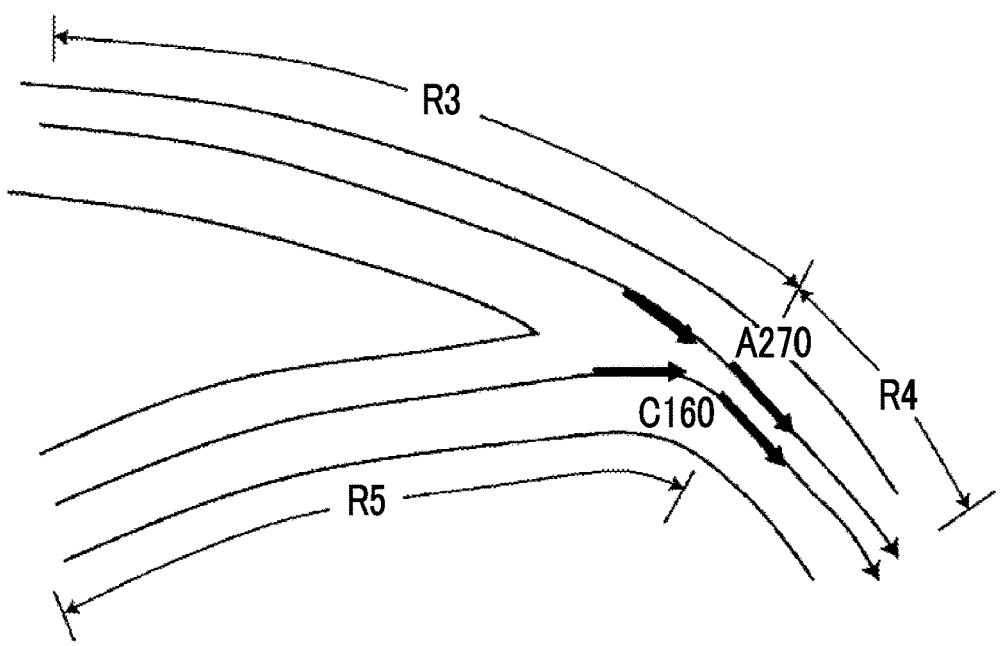
FIG. 10B illustrates an example of the streamline in a case in which the blood vessel joins.

Next, a portion in which the blood vessels join will be described. As illustrated in FIG. 5B, "A270" and "C160" are connection portions and a voxel to which route position information connected to "A270" is assigned and a voxel to which route position information connected to "C160" is assigned are present in the vicinity of the connection portions. The streamlines connected to "A270" and "C160" include a streamline connected in the direction from the blood vessel region R3 to the blood vessel region R4 and a streamline connected in the direction from the blood vessel region R5 to the blood vessel region R4 according to whether there is a voxel to which route position information connected to "A270" is assigned or a voxel to which route position information connected to "C160" is assigned in the direction indicated by the three-dimensional flow velocity vector of each voxel. FIG. 10B illustrates an example in which two streamlines from the connection portions "A270" and "C160" join into one blood vessel.

As described above, a streamline is generated by connecting only the three-dimensional flow velocity vectors of the voxels whose route position information is sequentially arranged in a case in which the three-dimensional flow velocity vector is traced. As such, the assignment of the route position information makes it possible to prevent the streamline that enters the blood vessel region R2 from the blood vessel region R1 across the blood vessel wall from being drawn. In the drawing of the path line or the streak line, the same determination as described above is performed to prevent a trajectory from being drawn across the blood vessel wall. This holds for drawing using a particle tracking method.

The case in which the three-dimensional flow velocity vector is acquired from the volume data captured by the three-dimensional cine phase contrast magnetic resonance method has been described above. Blood flow analysis using computational fluid dynamics (CFD) may be performed using the blood vessel region extracted by the blood vessel region extraction unit 11 to acquire the flow velocity vector. For example, blood flow analysis can be performed using blood vessel regions extracted from each of the CT images captured in time series. Specifically, a contrast-enhanced CT image or a contrast-enhanced MRI image can be used.

The image acquisition unit 10 may acquire a three-dimensional ultrasound image captured in time series by Doppler measurement and a flow velocity vector may be acquired using velocity information in the blood vessel region acquired on the basis of the ultrasound image.

The morphological image generation unit 15 performs a volume rendering process for a CT image or an MRI image to generate a morphological image. In a case in which a morphological image is generated, particularly, it is desirable to generate a morphological image, using an image in which a blood vessel region and other regions are clearly distinguished from each other, such as a contrast-enhanced CT image or a contrast-enhanced MRI image.

The drawing unit 13 displays a trajectory indicating a blood flow, such as the streamline, the path line, or the streak line, so as to be superimposed on the morphological image generated by the morphological image generation unit 15. Alternatively, the movement aspect of particles obtained by the particle tracking method is drawn so as to be superimposed on the morphological image.

Figure 11:
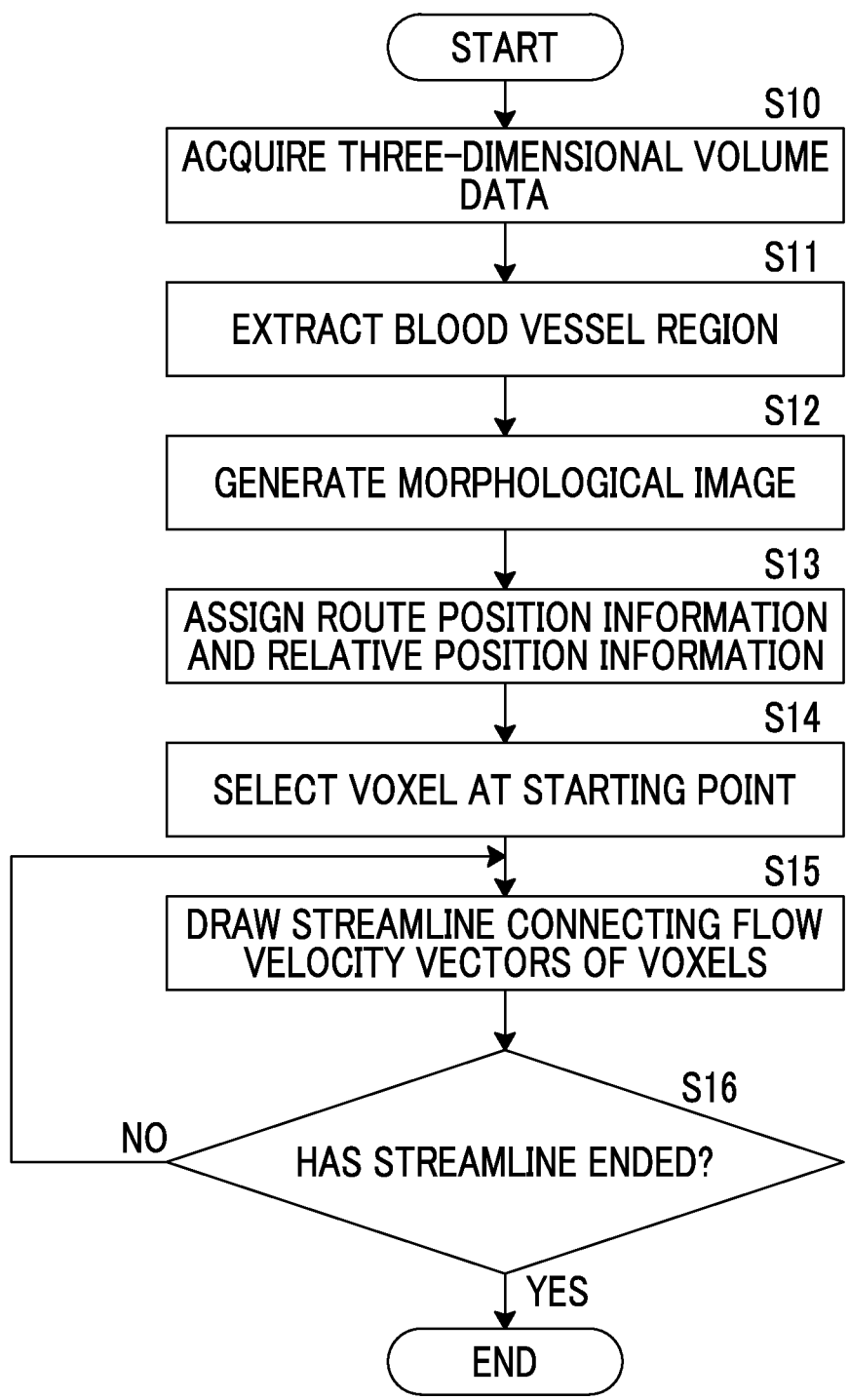
FIG. 11 is a flowchart illustrating the flow of a process of the fluid analysis apparatus according to the invention.

Next, the flow of a process of the fluid analysis apparatus according to this embodiment will be described with reference to a flowchart illustrated in FIG. 11.

First, the image acquisition unit 10 acquires two kinds of three-dimensional volume data of a contrast-enhanced CT image of a patient and an MRI image captured by the three-dimensional cine phase contrast magnetic resonance method in response to, for example, the input of settings, such as the identification information of the patient, by the user (S10).

Then, the blood vessel region extraction unit 11 extracts a blood vessel region from the contrast-enhanced CT image of the chest acquired by the image acquisition unit 10 (S11). In addition, the morphological image generation unit 15 generates a morphological image (S12).

The assignment unit 12 assigns route position information and relative position information along the route of the blood vessel region extracted by the blood vessel region extraction unit 11 (S13).

The drawing unit 13 selects a voxel as a starting point (S14), selects the next voxel according to the route position information of the voxel assigned by the assignment unit 12 and the direction of the three-dimensional flow velocity vector acquired by the vector acquisition unit 14 from the three-dimensional volume data of the MRI image captured by the three-dimensional cine phase contrast magnetic resonance method, and draws a streamline connecting the flow velocity vectors of the voxels (S15). Until the streamline ends (S16-NO), the drawing unit 13 draws streamlines connecting the flow velocity vectors of the voxels while tracing the voxels on the basis of the route position information and the direction of the three-dimensional flow velocity vector (S15). In addition, in the connection portion in which the blood vessel is branched or joins, streamlines are connected using the relative position information and the route position information of the blood vessels.

In a case in which there is a voxel that is not continuous with the route position information, the drawing unit 13 ends the drawing of the streamline. Alternatively, in a case in which the blood vessel region ends, the drawing unit 13 ends the drawing of the streamline (S16—YES).

In the above-described embodiment, as illustrated in FIG. 9, since the streamline is drawn without passing through the blood vessel wall, it is easy to understand the flow of blood. As such, the fluid analysis apparatus makes it easy to check the flow of blood. Therefore, it is possible to observe a portion in which blood flows backward in the artery coming out of the heart or a portion in which blood flows in a spiral shape in the aneurysm, which makes it easy to perform a diagnosis.

In the above-described embodiment, the case in which a blood flow is analyzed has been described. However, the anatomical structure may be a region in which cerebrospinal fluid flows, such as the brain, and the fluid may be cerebrospinal fluid. In a case in which the anatomical structure is the brain, the morphological image generation unit 15 generates a morphological image obtained by performing volume rendering for the brain. The image in which the flow of, for example, the streamline can be recognized is displayed so as to be superimposed on the generated morphological image.

The case in which a streamline is drawn has been described in detail above. However, even in a case in which a path line, a streak line, or an image generated by the particle tracking method is drawn, the route position information and the relative position information may be assigned along the route of the blood vessel, which makes it possible to prevent a flow from passing through the blood vessel wall and to accurately check a blood flow.

The case in which one computer functions as the fluid analysis apparatus has been described above. However, the functions of the fluid analysis apparatus may be dispersed to a plurality of computers. For example, another computer only for image processing may extract an anatomical structure and/or generate a morphological image and a computer that displays the result of the fluid analysis process may receive the information of the anatomical structure and/or the morphological image from the computer only for image processing, display the morphological image, and display the representative two-dimensional flow velocity vector so as to be superimposed on the morphological image.

The case in which a general-purpose computer functions as the fluid analysis apparatus has been described above. However, a dedicated computer may function as the fluid analysis apparatus. The dedicated computer may be firmware that executes a program recorded on a non-volatile memory, such as a built-in read only memory (ROM) or a flash memory. Furthermore, a dedicated circuit, such as an application specific integrated circuit (ASIC) or a field programmable gate array (FPGA) that permanently stores a program for implementing at least some of the functions of the fluid analysis apparatus, may be provided. Alternatively, program commands that are stored in a dedicated circuit may be combined with program commands which are executed by a general-purpose CPU programmed to use a program of the dedicated circuit. As described above, program commands may be executed by any combination of the hardware configurations of the computers.

EXPLANATION OF REFERENCES

1: fluid analysis apparatus
2: medical image storage server
3: imaging apparatus
4: network
6: three-dimensional volume data
10: image acquisition unit
11: structure extraction unit
12: assignment unit
13: drawing unit
14: vector acquisition unit
15: morphological image generation unit

What is claimed is:

1. A fluid analysis apparatus comprising:
a storage medium for storing at least an image which has been captured, and
a processor coupled to the storage medium and configured to:
acquire from three-dimensional volume data obtained by the image of an object including an anatomical structure in which a fluid flows, information of a three-dimensional flow velocity vector indicating a flow velocity of the fluid in the anatomical structure for each voxel and assigns route position information capable of identifying an order along a route of the anatomical structure to each position in the anatomical structure;
select the three-dimensional flow velocity vector such that route position information of a position where the three-dimensional flow velocity vector is present is sequentially arranged from one point in the anatomical structure and draws a trajectory indicating a flow of the fluid so as to be visibly recognized; and
determine whether a first voxel of the three-dimensional volume data indicates the route of the anatomical structure or a different route of another anatomical structure based on whether a first route position information corresponding to the first voxel is continuous or sequentially arranged with respect to a second route position information corresponding to a second voxel, wherein the first voxel and the second voxel are adjacent to each other, and the route of the anatomical structure is not connected to the different route of the another anatomical structure between the first voxel and the second voxel.

2. The fluid analysis apparatus according to claim 1,
wherein the processor is configured to extract a center line of the anatomical structure, assign route position information along the center line, and assign the same route position information as the route position information assigned to the center line to each position in a cross section perpendicular to the center line of the anatomical structure.

3. The fluid analysis apparatus according to claim 2,
wherein the processor is configured to assign the same route position info i ration as the route position information assigned along the center line of the anatomical structure closest to the three-dimensional flow velocity vector in the anatomical structure.

4. The fluid analysis apparatus according to claim 1,
wherein the processor is configured to draw the trajectory on a morphological image obtained by projecting a morphology of the anatomical structure to a projection plane so as to be visibly recognized.

5. The fluid analysis apparatus according to claim 2,
wherein the processor is configured to draw the trajectory on a morphological image obtained by projecting a morphology of the anatomical structure to a projection plane so as to be visibly recognized.

6. The fluid analysis apparatus according to claim 3,
wherein the processor is configured to draw the trajectory on a morphological image obtained by projecting a morphology of the anatomical structure to a projection plane so as to be visibly recognized.

7. The fluid analysis apparatus according to claim 1, wherein, before and after a connection portion in which the anatomical structure is branched or joins, the processor is configured to assign relative position information indicating a connection relationship between a route before branching and a plurality of routes after the branching or a connection relationship between a plurality of routes before joining and a route after the joining, and
the processor configured to draw the trajectory so as to be visibly recognized on the basis of the route position information and the relative position information.

8. The fluid analysis apparatus according to claim 2, wherein, before and after a connection portion in which the anatomical structure is branched or joins, the processor is configured to assign relative position information indicating a connection relationship between a route before branching and a plurality of routes after the branching or a connection relationship between a plurality of routes before joining and a route after the joining, and
the processor configured to draw the trajectory so as to be visibly recognized on the basis of the route position information and the relative position information.

9. The fluid analysis apparatus according to claim 3, wherein, before and after a connection portion in which the anatomical structure is branched or joins, the processor is configured to assign relative position information indicating a connection relationship between a route before branching and a plurality of routes after the branching or a connection relationship between a plurality of routes before joining and a route after the joining, and
the processor configured to draw the trajectory so as to be visibly recognized on the basis of the route position information and the relative position information.

10. The fluid analysis apparatus according to claim 4, wherein, before and after a connection portion in which the anatomical structure is branched or joins, the processor is configured to assign relative position information indicating a connection relationship between a route before branching and a plurality of routes after the branching or a connection relationship between a plurality of routes before joining and a route after the joining, and
the processor configured to draw the trajectory so as to be visibly recognized on the basis of the route position information and the relative position information.

11. The fluid analysis apparatus according to claim 5, wherein, before and after a connection portion in which the anatomical structure is branched or joins, the processor is configured to assign relative position information indicating a connection relationship between a route before branching and a plurality of routes after the branching or a connection relationship between a plurality of routes before joining and a route after the joining, and
the processor configured to draw the trajectory so as to be visibly recognized on the basis of the route position information and the relative position information.

12. The fluid analysis apparatus according to claim 1, wherein the three-dimensional flow velocity vector is obtained from three-dimensional volume data captured by a three-dimensional cine phase contrast magnetic resonance method.

13. The fluid analysis apparatus according to claim 1, wherein the anatomical structure is a blood vessel, the fluid is blood, and the three-dimensional flow velocity vector is a flow velocity vector of the blood.

14. The fluid analysis apparatus according to claim 13, wherein the three-dimensional flow velocity vector is obtained by a result of a blood flow analysis simulation.

15. The fluid analysis apparatus according to claim 1, wherein the fluid is cerebrospinal fluid and the three-dimensional flow velocity vector is a flow velocity vector of the cerebrospinal fluid.

16. The fluid analysis apparatus according to claim 1, wherein the trajectory is a streamline, a path line, or a streak line.

17. The fluid analysis apparatus according to claim 1, wherein the trajectory is drawn by a particle tracking method.

18. A method for operating the fluid analysis apparatus comprising a storage medium for storing at least an image which has been captured and a processor coupled to the storage medium, the method comprising:
acquiring, from the storage medium by a processor, from three-dimensional volume data obtained by the image of an object including an anatomical structure in which a fluid flows, information of a three-dimensional flow velocity vector indicating a flow velocity of the fluid in the anatomical structure for each voxel and assigns route position information capable of identifying an order along a route of the anatomical structure to each position in the anatomical structure;
selecting, by the processor, the three-dimensional flow velocity vector such that route position information of a position where the three-dimensional flow velocity vector is present is sequentially arranged from one point in the anatomical structure and draws a trajectory indicating a flow of the fluid so as to be visibly recognized; and
determining, by the processor, whether a first voxel of the three-dimensional volume data indicates the route of the anatomical structure or a different route of another anatomical structure based on whether a first route position information corresponding to the first voxel is continuous or sequentially arranged with respect to a second route position information corresponding to a second voxel, wherein the first voxel and the second voxel are adjacent to each other, and the route of the anatomical structure is not connected to the different route of the another anatomical structure between the first voxel and the second voxel.

19. A non-transitory computer readable recording medium storing a fluid analysis program that causes a computer comprising a storage medium for storing at least an image which has been captured and a processor coupled to the storage medium to perform functions as a fluid analysis apparatus, the functions comprising:
acquiring, from the storage medium by a processor, from three-dimensional volume data obtained by the image of an object including an anatomical structure in which a fluid flows, information of a three-dimensional flow velocity vector indicating a flow velocity of the fluid in the anatomical structure for each voxel and assigns route position information capable of identifying an order along a route of the anatomical structure to each position in the anatomical structure;
selecting, by the processor, the three-dimensional flow velocity vector such that route position information of a position where the three-dimensional flow velocity vector is present is sequentially arranged from one point in the anatomical structure and draws a trajectory indicating a flow of the fluid so as to be visibly recognized; and determining, by the processor, whether a first voxel of the three-dimensional volume data indicates the route of the anatomical structure or a different route of another anatomical structure based on whether a first route position information corresponding to the first voxel is continuous or sequentially arranged with respect to a second route position information corresponding to a second voxel, wherein the first voxel and the second voxel are adjacent to each other, and the route of the anatomical structure is not connected to the different route of the another anatomical structure between the first voxel and the second voxel.

20. A fluid analysis apparatus comprising:
a memory that stores commands to be executed by a computer; and
a processor that is configured to execute the stored commands,
wherein the processor performs
a process of acquiring, from three-dimensional volume data obtained by capturing an image of an object including an anatomical structure in which a fluid flows, information of a three-dimensional flow velocity vector indicating a flow velocity of the fluid in the anatomical structure for each voxel and assigning route position information capable of identifying an order along a route of the anatomical structure to each position in the anatomical structure, a process of selecting the three-dimensional flow velocity vector such that route position information of a position where the three-dimensional flow velocity vector is present is sequentially arranged from one point in the anatomical structure and drawing a trajectory indicating a flow of the fluid so as to be visibly recognized; and a process of determining whether a first voxel of the three-dimensional volume data indicates the route of the anatomical structure or a different route of another anatomical structure based on whether a first route position information corresponding to the first voxel is continuous or sequentially arranged with respect to a second route position information corresponding to a second voxel, wherein the first voxel and the second voxel are adjacent to each other, and the route of the anatomical structure is not connected to the different route of the another anatomical structure between the first voxel and the second voxel.

21. The fluid analysis apparatus according to claim 1, wherein the anatomical structure is a blood vessel, and the processor is configured to determine whether the first route position information is sequentially arranged with respect to the second route position information on the basis of the size of the voxels and the width of the blood vessel.

* * * * *